(12) United States Patent
Iversen

(10) Patent No.: US 8,070,822 B1
(45) Date of Patent: Dec. 6, 2011

(54) TOOL FOR CONTROLLING THE MUTUAL ANGLE BETWEEN THE PARTS OF AN ARTIFICIAL HIP JOINT

(75) Inventor: Bjørn Franc Iversen, Oslo (NO)

(73) Assignee: OM Surgical (UK) Limited, London (GB)

( * ) Notice: Subject to any disclaimer, the term of this patent is extended or adjusted under 35 U.S.C. 154(b) by 0 days.

(21) Appl. No.: 10/099,010

(22) PCT Filed: Sep. 13, 2000

(86) PCT No.: PCT/NO00/00299
§ 371 (c)(1),
(2), (4) Date: Mar. 13, 2002

(87) PCT Pub. No.: WO01/19296
PCT Pub. Date: Mar. 22, 2001

(30) Foreign Application Priority Data

Sep. 13, 1999 (NO) .................................... 19994445

(51) Int. Cl.
*A61F 2/36* (2006.01)
(52) U.S. Cl. .................. 623/22.12; 606/100; 606/99
(58) Field of Classification Search .................. 606/99, 606/91, 81, 104; 623/20.35, 20.3, 22.12, 623/22.11
See application file for complete search history.

(56) References Cited

U.S. PATENT DOCUMENTS

| | | | | |
|---|---|---|---|---|
| 3,656,184 A | * | 4/1972 | Chambers | 623/22.15 |
| 3,801,989 A | * | 4/1974 | McKee | 623/22.12 |
| 4,222,382 A | * | 9/1980 | Antonsson et al. | 606/100 |
| 4,457,306 A | * | 7/1984 | Borzone | 606/1 |
| 4,632,111 A | | 12/1986 | Roche | |
| 4,642,121 A | * | 2/1987 | Keller | 623/22.12 |
| 5,540,697 A | | 7/1996 | Rehmann et al. | 606/91 |
| 5,976,149 A | | 11/1999 | Masini | 606/91 |
| 6,203,575 B1 | * | 3/2001 | Farey | 623/18.11 |

FOREIGN PATENT DOCUMENTS

| | | |
|---|---|---|
| EP | 027873 | 6/1986 |
| EP | 0 865 776 A2 | 9/1998 |

(Continued)

OTHER PUBLICATIONS

European Search Report.

(Continued)

*Primary Examiner* — Brian E. Pellegrino
*Assistant Examiner* — Christopher D Prone
(74) *Attorney, Agent, or Firm* — Peter F. Corless; Christine C. O'Day; Edwards Wildman Palmer LLP

(57) ABSTRACT

A method for controlling the mutual angle between the parts of an artificial hip joint during an operation for insertion of the artificial hip joint, is described. The stem of the femoral hip prosthesis is fastened permanently or removable in the usual manner in the proximal end of the femur. A tool for controlling of the mutual angle between the stem of the prosthesis and the cup of the prosthesis is fastened to the stem. The femur of the patient is then oriented in a predefined position and the cup is then brought into its intended position by means of the femur of the patient and the mentioned tool. A tool for controlling the mutual angle between the parts of the artificial hip joint is also described.

15 Claims, 8 Drawing Sheets

FOREIGN PATENT DOCUMENTS

| | | |
|---|---|---|
| EP | 0 888 759 A1 | 1/1999 |
| GB | 2 197 790 A | 11/1986 |
| GB | 2 224 937 A | 5/1990 |
| JP | S62-502241 A | 9/1987 |
| JP | 04-044758 A | 2/1992 |
| JP | 05-123334 A | 5/1993 |
| JP | 09-098994 A | 4/1997 |
| WO | WO 91/06263 | 5/1991 |
| WO | WO 94/12109 * | 6/1994 |

OTHER PUBLICATIONS

Sulzer Orthopedics, "Joint Care/Fracture Care", Anatomical Shoulder-Cemented Shoulder Prosthesis, Product Information and Surgical Technique, Copyright 2000 by Sulzer Orthopedics Ltd., Baar Switzerland.

Japanese Official Action for JP Appln No. 2001-522935, dated Apr. 15, 2008.

* cited by examiner

TOOL FOR CONTROLLING THE MUTUAL ANGLE BETWEEN THE PARTS OF AN ARTIFICIAL HIP JOINT

PRIORITY CLAIMED

This application claims the first priority of Norway application no. 1999 4445 filed on Sep. 13, 1999.

BACKGROUND

The present invention regards the area of orthopaedic surgery, and in particular a method of and devices for ensuring that prosthesis components are inserted correctly upon implantation of artificial hip joints into humans. In particular, the invention is directed at a method of and devices for ensuring the correct mutual positioning of the prosthesis components.

An artificial hip joint has two main components; a prosthesis stem and a cup. One end of the prosthesis stem is provided either with a spherical ball head or a prosthesis neck on which can be placed a ball head, where the ball head is designed for a close, sliding fit in a spherical recess in the cup. Together, the prosthesis stem with the ball head and the cup will act as a ball joint to replace the natural ball joint.

The other end of the prosthesis stem comprises an elongated part designed to be attached to the hollow femoral canal in the patient's femur.

The cup is designed to be attached to the cavity on the patient's pelvis. The hemispherical shaped recess in the cup is linked with an exterior surface designed to be attached to the pelvis, via a side face. The exterior surface may have various shapes, all according to the method of attachment to the pelvis and other choices made by the supplier. Several of the cups that are in use are shaped as an approximate hemisphere, where the outer hemispherical surface is designed to be cemented to the pelvis. The side face that connects the recess and the exterior surface may be flat or possibly inwardly sloping towards the recess, which is preferably approximately centred in the side face.

The prosthesis stem and the cup may be fixed to the femur and the pelvis respectively by using cement, or through a cement-free force fit. The invention may be used with both fixation techniques.

When replacing a worn out hip with a prosthesis, the head of the femur is replaced. This is done by cutting the neck of the femur and hollowing out the top of the femoral canal in order to make room for the elongated prosthesis stem that is either cemented into the hole or force fitted.

The cavity on the pelvis is milled out to receive the cup, which is then fixed either by means of cement or a force fit.

If the ball head is detachable, this is placed on the prosthesis stem before the ball head is placed in the cup, the joint is assembled by lifting the patient's leg up to a natural position and inserting the ball head in the recess in the cup, whereupon the incision is closed.

Such a prosthesis should give the patient a mobility that approximates that which is provided by the natural joint. Moreover, it is important that a "natural" movement of the joint does not cause the patient to get in a situation where the leg ends up in positions where the neck of the prosthesis rides on the edge of the cup. This may cause luxation of the joint, where the head of the prosthesis jumps out of the cup. This happens through simple leverage. Luxation occurs in the case of between 3 and 10% of all patients who have had a femoral prosthesis put in. If this happens, the patient must be anaesthetised before the joint is put back into place. Some patients must have a new operation. The risk of luxation is much greater in patients whose prosthesis components are assembled so as to have an incorrect mutual positioning, than in those where the mutual positioning of the components is correct.

The inventor has previously shown that an optimum mutual relationship between the prosthesis stem and the cup under experimental conditions (not published) results in a reduced risk of luxation because the patient can go through the everyday natural range of motion (ROM) without the parts of the prosthesis ending up in such mutual positioning so as to entail a risk of luxation.

The inventor has previously shown (not published) that the most adequate ROM is achieved by assembling both prosthesis components in a manner so as to give them a forward angle of about 15 degrees relative to the frontal plane of the body, while the cup forms an angle of 45 degrees with the horizontal plane. In medical terminology, forward angling is termed anteversion.

The inventor has also previously shown (not published) that even though the optimum is to have each of the components angled forwards at 15 degrees, the result is nearly as good if the sum of the forward angling of the two components is 30 degrees. Thus a prosthesis joint where the cup is angled forwards at 5 degrees and the prosthesis stem is angled forwards at 25 degrees will result in a ROM for the patient that is nearly as adequate as if both components were angled forward at 15 degrees, the sum of the forward angling being 30 degrees is both cases Today there are no means available to ensure that the surgeon installs the prosthesis components with this correct mutual relationship. With today's methods therefore, this is done as judged by the eye. This judgement may be sufficient, especially for experienced surgeons who carry out a considerable number of this type of operation each year. It is estimated that 80% of all implantations of artificial hip joints are carried out by surgeons who do less than 20 of these every year. This number is not sufficient to get enough practice. It is therefore desirable to have a method and means that ensure a correct mutual positioning of the main parts of the prosthesis in order to reduce the possibility of errors, and thereby also reduce the risk of luxation with the resulting pain for the patient, and a possible second operation.

SUMMARY OF THE DISCLOSURE

The object of the present invention is to provide a method of ensuring the correct mutual positioning upon assembly of the prosthesis components.

According to the inventor, this is achieved by a method of ensuring the desired mutual positioning of the main parts of an artificial hip joint, i.e. a prosthesis stem with a ball head and a cup with a recess for receiving the ball head, where the prosthesis stem or a temporary prosthesis stem is fixed permanently or removably to the femur in the normal manner, and the cup is placed on the pelvis, where a tool for checking the mutual angle between the prosthesis stem and the cup is placed on the prosthesis stem, that the femur in the leg that is undergoing surgery is then oriented in a pre-determined position, and that the cup is placed in its final, desired position by means of the patient's femur with the prosthesis stem and the tool.

If the cup is fixed with cement, it is preferable that the femur be kept in this position until the cement for fixing the cup has set sufficiently.

In addition, it is an object of the present invention to provide means of ensuring that prosthesis components are assembled correctly in relation to each other.

This object is achieved by the provision of a tool for use during an operation for implantation of an artificial hip joint for controlling the mutual positioning of the main components in an artificial hip joint, i.e. a prosthesis stem with a neck in the patient's femur, and a cup in the patient's pelvic cavity, where a cutout and/or a bore has been formed in the tool, which cutout or bore is designed for engagement with a part of the prosthesis stem and or the neck of the prosthesis, and the tool also comprises one or more legs or abutment surfaces designed to abut at least a part of that part of the cup that links the exterior of the cup with the recess in the cup.

It is preferred that at least parts of the cutout or the bore are designed for non-rotating engagement with the prosthesis stem in order to prevent rotation of the tool relative to the prosthesis stem.

It is also preferred that the cutout or the bore is designed for rotating engagement with the neck of the prosthesis, and that the tool further comprises a handle by which the tool can be rotated to the desired position.

Furthermore it is preferred that it also comprises a guide head with a cutout or a bore designed to engage the neck of the prosthesis, and where the guide head matches the recess in the cup.

It is also preferred that the legs abutment surfaces that are designed to abut at least a part of that part of the cup that links the exterior of the cup with the recess in the cup, are an integrated part of the guide head.

It is further preferred that the legs or abutment surfaces that are designed to abut at least a part of that part of the cup that links the exterior of the cup with the recess in the cup, are removably mounted on the guide head.

It is also preferred that the legs or abutment surfaces that are designed to abut at least a part of that part of the cup that links the exterior of the cup with the recess in the cup, are a collar with a diameter that is greater than that of the recess in the cup.

According to a preferred embodiment the collar is removably mounted on the guide head.

Additionally it is preferred that the legs or the abutment surface are three or more legs designed to abut at least a part of that part of the cup that links the exterior of the cup with the recess in the cup.

It is also preferred that the legs may be withdrawn form abutment with the cup.

Finally it is preferred that when the tool is used, use is made of a prosthesis stem temporarily provided in the patient's femur.

BRIEF DESCRIPTION OF THE DRAWINGS

In the following, the invention will be described further with reference to the attached figures, in which.

DETAILED DESCRIPTION

Example 1

Figure 1:
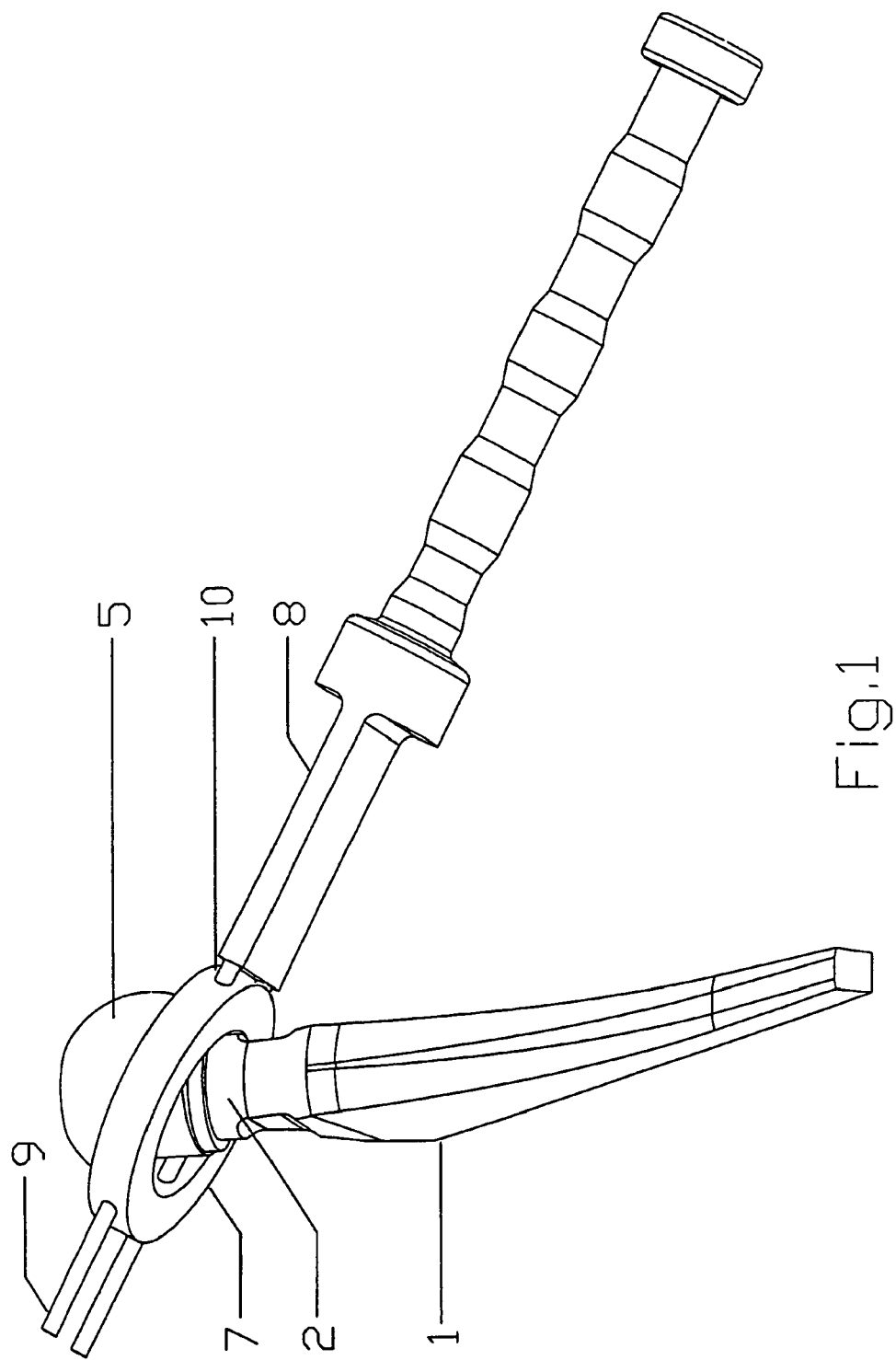
FIG. 1 shows a preferred embodiment of the present tool set on the neck of a prosthesis on the prosthesis stem.
Figure 2:
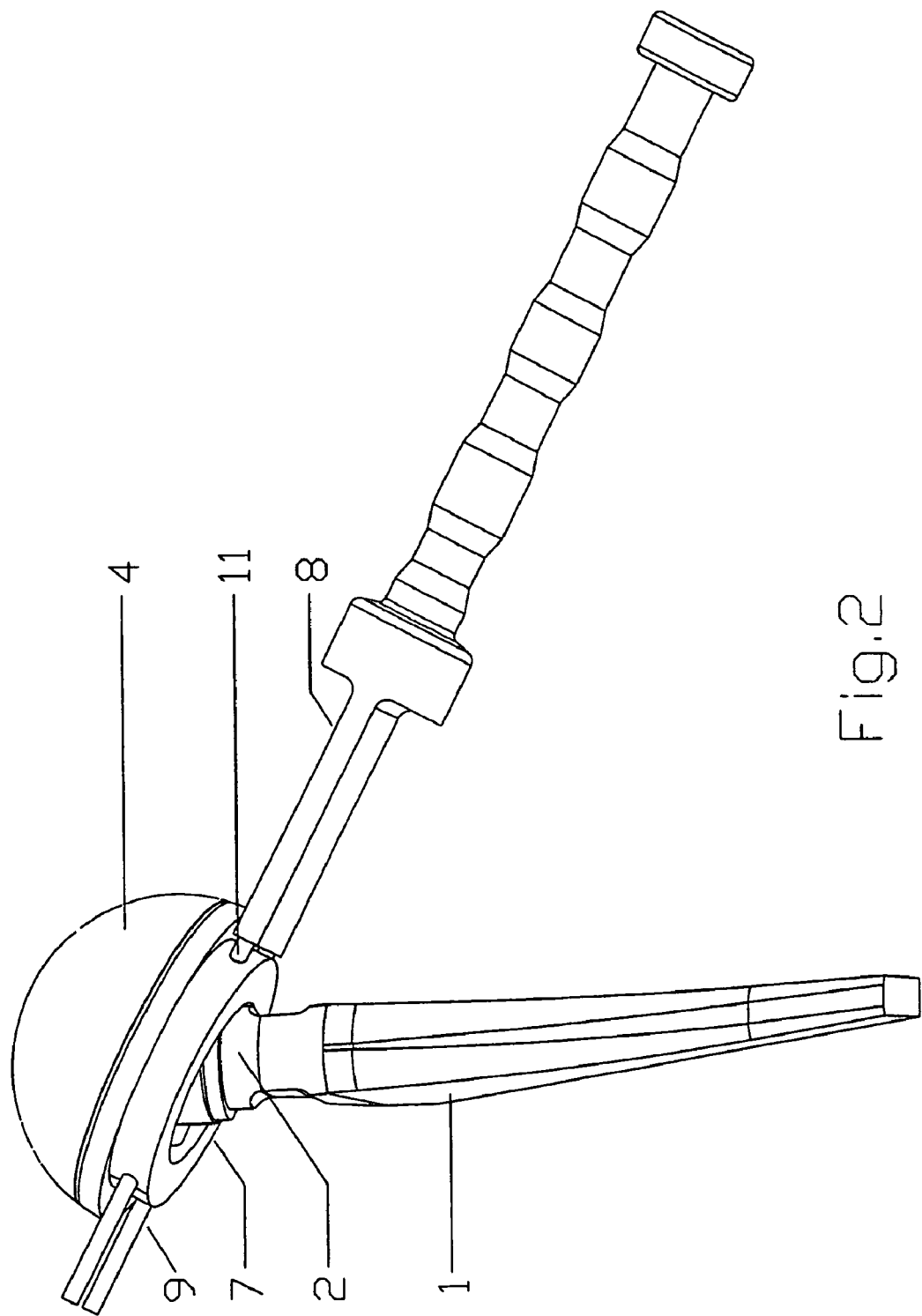
FIG. 2 shows the same embodiment as FIG. 1, in which the cup has been put on the tool.
Figure 3:
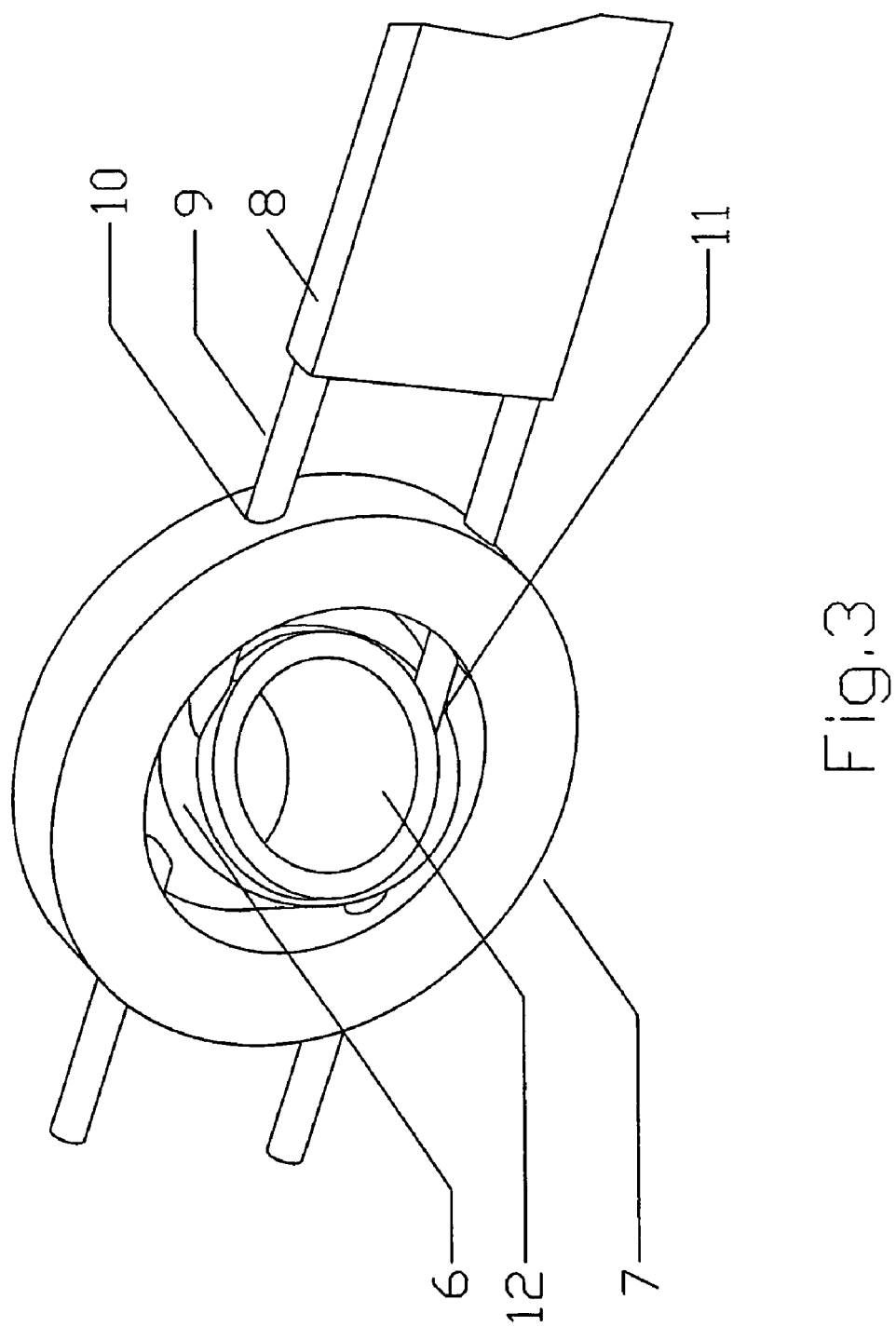
FIG. 3 shows the same tool as FIG. 1, seen from below.
Figure 4:
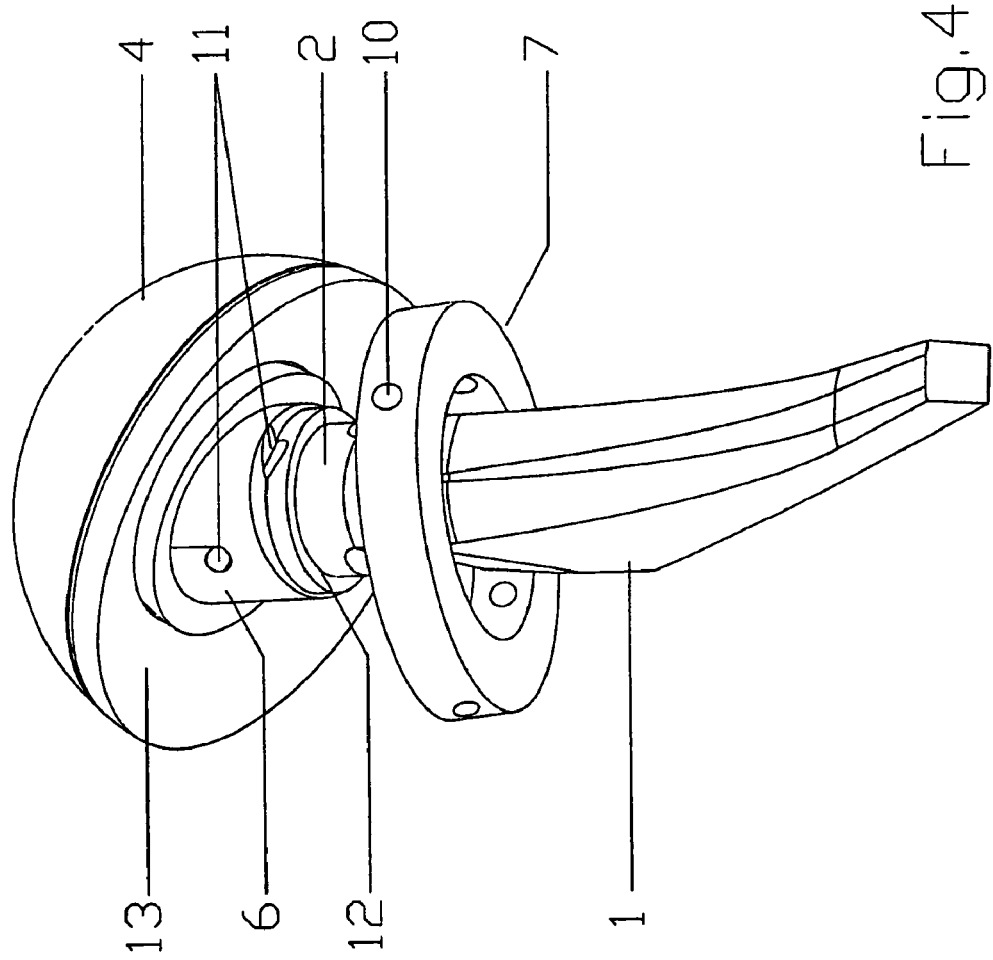
FIG. 4 shows the same tool as FIG. 1, partly disassembled.

Here, a first preferred embodiment of the present tool is used. For the most part, the operation is performed in the usual manner, apart from the fact that the present tool is used during positioning and fixing of the cup.

A typical artificial hip joint comprises a prosthesis stem with an elongated part at one end for fixing to the femur, and a neck designed to receive a ball head. The ball head, which is spherical, has a bore that is dimensioned so as to receive the neck of the prosthesis. The ball head is also designed for a close, sliding fit in a recess in the other main part of the femoral prosthesis, the cup 4. Prostheses are also available in which the ball head is rigidly mounted on the prosthesis stem, or the prosthesis stem and the ball head are formed as one piece.

The exterior surface of the cup 4 is designed to be cemented or otherwise fixed to the pelvis, while the part that links the exterior surface with the recess is normally a side face that faces away from the pelvis after assembly.

The embodiment of the tool shown in FIGS. 1-4 comprises three main components; a guide head comprising a hemispherical part that matches the recess in the cup 4, and an approximate neck 6 on which a collar 7 may be placed, the inner diameter of the collar corresponding to the outer diameter of the neck 6, and the outer diameter of the collar being greater than the diameter of the guide ball 5. In addition, there is a bore 12 in the neck 6 of the guide head, which bore is matched to the neck 2 of the prosthesis stem 1.

The third component of the tool is a handle 8 with two guide rods 9 designed to be put through guide holes 10 in the collar 7 and guide holes 11 in the neck 6 that are provided for this purpose, in order to lock these together when assembling the prosthesis.

When the tool has been assembled and the guide ball 5 is put into the recess in the cup 4, the collar 7 will rest against the side face 13 of the cup and thereby define the angle between the neck of the prosthesis and the cup.

The surgeon first mounts the prosthesis stem in the normal manner and fixes it in the final position in the femoral cavity, possibly by means of cement. Then the present tool is mounted on the neck 2 of the prosthesis, and the tool is used as an inserter, to force the cup 4 into the pelvic cavity, in a position that results in the desired total anteversion, preferably about 30 degrees.

The angles of the guide holes 10, 11 and the collar 7 is preferably defined in such a way relative to each other that, when orienting the tool for definition of the angle between the cup and the prosthesis stem, the tool is set so as to make the guide holes 10, 11 approximately normal on the coronal plane of the patient. The guide rods may be pulled out by use of the handle when the surgeon is satisfied with the positioning of the prosthesis components. By this means the collar 7 will move away from the cup, while the head remains in place in the cup. As the contact surface between the head and the cup is spherical, the prosthesis stem will not transfer small movements of the leg to the cup while the cement is hardening. Any movement of the cup in the hardening period will cause a weakening of the cement.

By using a cup for a force fit, the method will be more or less equal to that which is described above. Instead of holding the leg in a given position until the cement hardens, it is here necessary to keep the leg in the desired position until the cup has been forced partly or all the way into place. If the cup is forced partly into place while the leg is kept in the desired position, the final fixing must be carried out after the guide head has been removed and the joint has been luxated.

In the embodiment shown in FIGS. 1-4, the collar 7 is a ring. In an alternative tool, illustrated in FIGS. 5 and 6, the collar 7 is open, so as to make it possible to extract it fully from the area of surgery, to avoid it being left hanging around the neck of the prosthesis stem while the cement is hardening.

Figure 5:
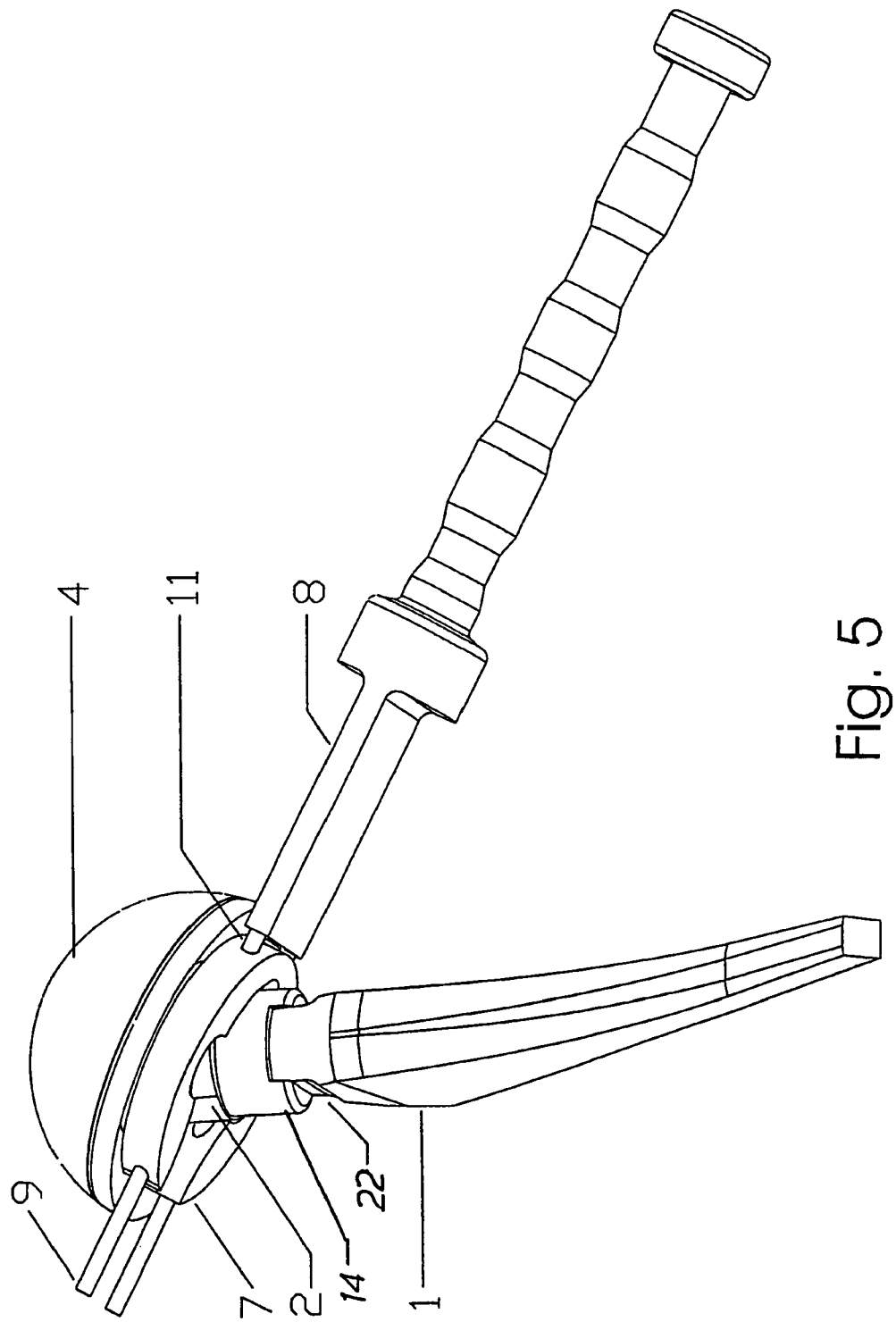
FIG. 5 shows an alternative embodiment.
Figure 6:
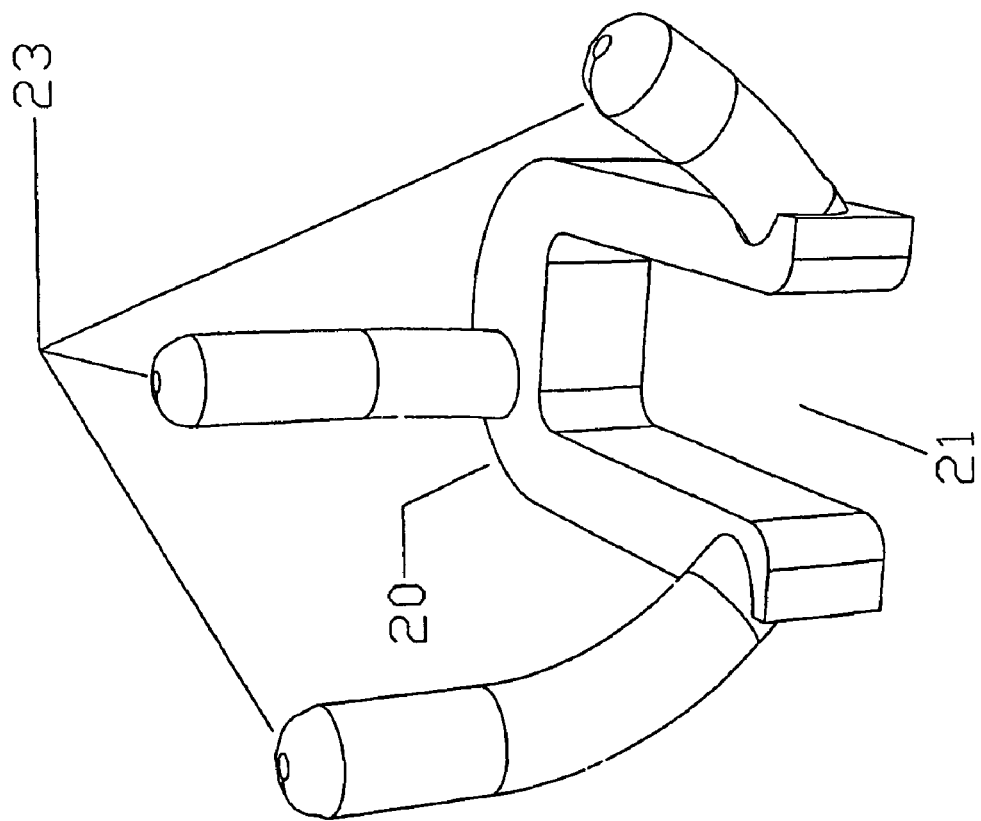
FIG. 6 shows an alternative tool according to the invention.

Furthermore, on the tool shown in FIGS. 5 and 6, the guide ball is extended by an extension 14 that encompasses the upper part of the prosthesis stem. The sides of this upper part are flat, so as to prevent the guide ball 5 and the collar 7 from rotating about the neck of the prosthesis stem. Thus it will not be necessary to use a handle 8 for controlling these as mentioned above. In this embodiment the guide rods 9 are replaced either by separate guide rods or a bow 15 running though the collar 7 and the guide ball 5.

The tool as described may be made from various materials, such as plastic or metal. A simpler tool than the one described may be a tool in which the collar 7 and the guide head 5 is an integrated unit.

The guide head is shown as an approximate hemisphere with a flattened top. This flattening makes it easier to assemble the prosthesis under the above described procedure, however it is not necessary for the invention. It is also not necessary for the guide ball to be hemispherical. The important thing is for it to be designed to engage the recess in the cup without any play. In order to avoid touching the edges of the cup when inserting the guide head into the recess, and thereby moving the cup, the guide head may as an example be cone shaped.

Example 2

Figure 7:
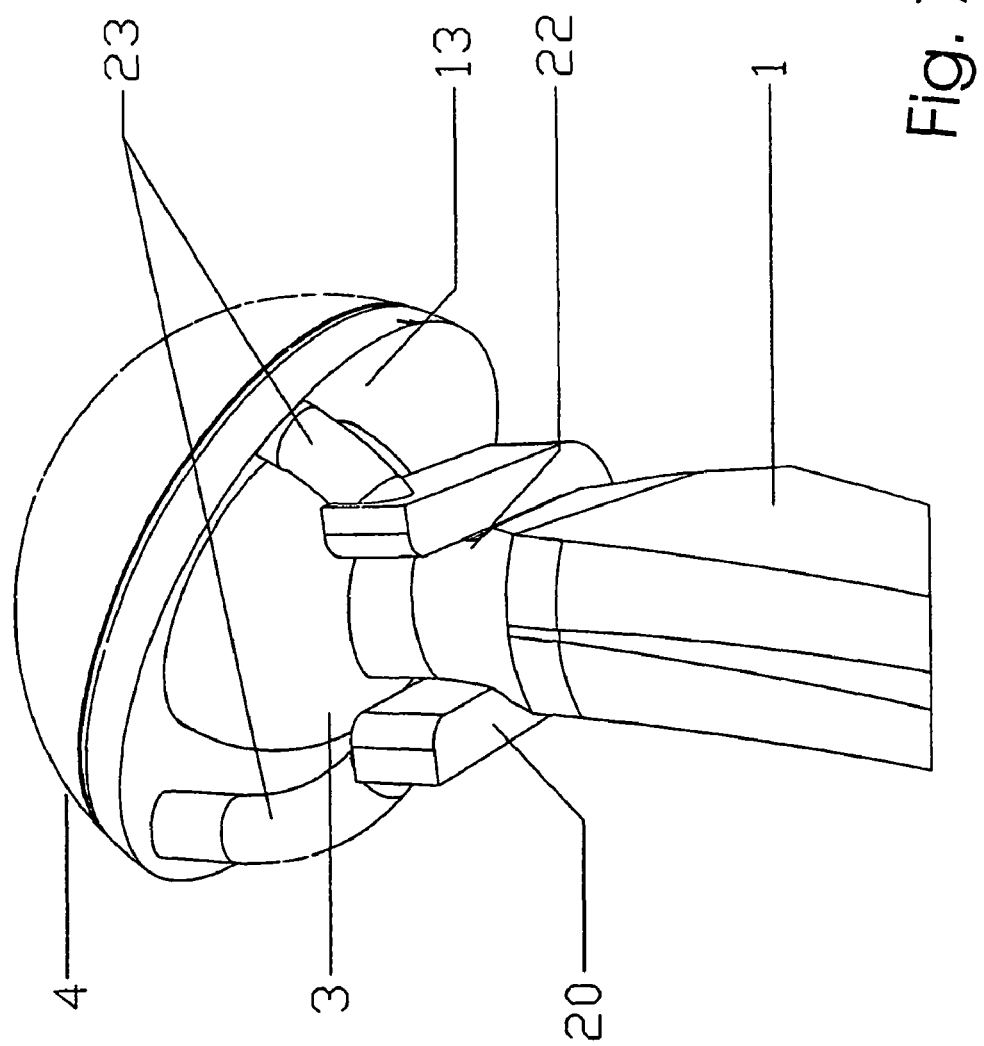
FIG. 7 shows the tool of FIG. 6 set on the prosthesis stem.
Figure 8:
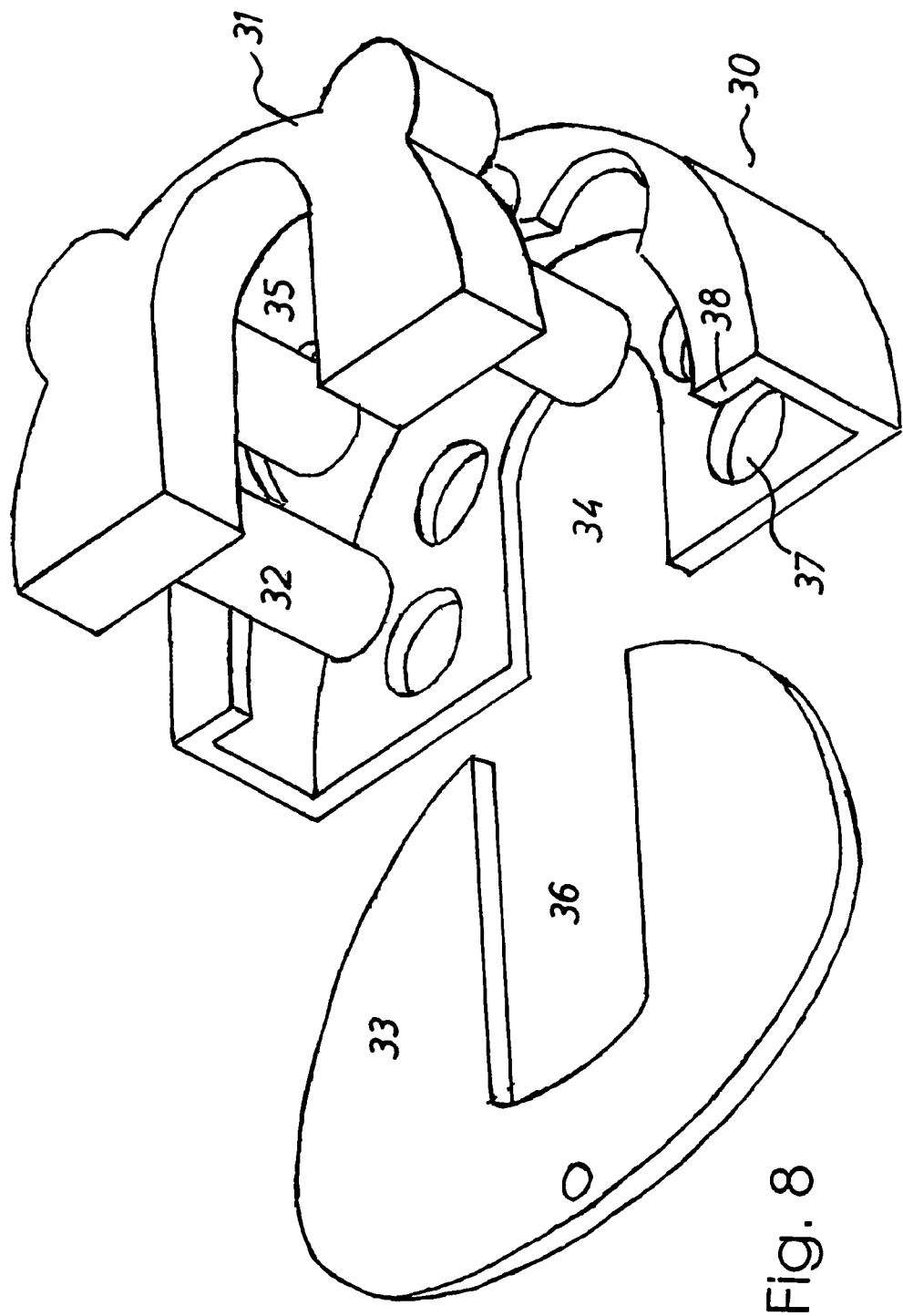
FIG. 8 shows an alternative embodiment of the present tool, where the tools parts are disassembled.

FIGS. 7 and 8 show another preferred embodiment of the present tool. This tool comprises a body 20 with a cutout 21 designed to engage a corresponding and pre-existing groove 22 in the prosthesis stem 1. Three legs 23 project from the body, which legs are designed to abut the part of the ball that lies between the exterior surface and the recess, i.e. side face 13.

The illustrated tool is also designed to partly enclose the head 3 of the prosthesis, so as to make the head 3 stay on the prosthesis stem 2 during implementation of a method that is essentially like the one described in example 1 above, for definition of the mutual angle between the prosthesis stem and the cup. This device may therefor also be used on a prosthesis stem with a fixed head.

It may be preferable to provide in this tool means such as a screw that may be used to ensure that the tool does not fall off the prosthesis stem during an operation.

In addition to the embodiments shown, other embodiments of the present tool may also be envisaged, by which the same object is achieved in an analogous manner. As an example, a tool may be envisaged that is attached to the prosthesis stem in the same manner as that described in example 2, where the tool has e.g. three legs designed to be temporarily attached to the cup, without making use of a separate guide head or possibly the ball head of the prosthesis in order to ensure the correct mutual positioning of the prosthesis stem and the cup.

Example 3

FIG. 8 shows an additional embodiment of the present tool. This embodiment might be regarded as a variation of the tool illustrated in FIGS. 6 and 7, where the tool comprises more parts that may be disassembled. The tool according to this embodiment comprises an outer part 30 and a inner part 31 with legs 32, and a locking plate 33.

When the tool is assembled the inner part will be situated stable in a cavity or a cutout in the outer part 30. The inner part 31 and the outer part 30 is kept together by means of a locking plate 33 that in the illustrated embodiment is placed between the top of the inner part and a rim 38 of the outer part 30. The locking plate 33, however, might have another shape and may lock the inner and outer parts together in other ways known by the skilled man in the art. As an example the rim 38 may be replaced by a number of tongues or by a groove in the outer part 30. The locking plate may also be replaced by locking pins that is inserted into bores through both the outer and inner parts.

When the tool is assembled the legs 32 will protrude out of bores 37 in the outer part 30. The legs 32 at the inner part 31 do usually have different length according to the desired angle between the prosthesis stem 1 and the cup 4. Preferably the legs 32 are slightly conical so that the play between the legs 32 and the bores 37 is as small as possible at the same time as the tools are to be easy to take apart.

The tool will keep the angle between the prosthesis stem 1 and the cup 4 fixed when the tool and a artificial hip prosthesis is assembled, as a cutout 34, 35, 36 in the outer part 30, the inner part 31 and the locking plate, respectively, is engaged with the prosthesis stem 1, e.g. with the groove 22 as illustrated in FIG. 8, to hold on and prevent rotation of the tool, and keep sure that the legs 32 bear against the side face 13 of the cup 4.

The procedure during the operation is as described in the previous examples. To prevent that small movement in the femur of the patient during the hardening of the cement, it is as mentioned above, advantageous to terminate the locking after the cup 4 is in the right position. The locking plate is then removed form the tool. The inner part 31 will then slide back so that no forces are transferred from prosthesis stem 1 to the cup 4 during the tome for hardening of the cement. If required a spring or the like might be provided to make sure that the inner part glides back when the locking plate is removed.

The illustrated tool has four legs but the number of legs may differ. Such a tool must have at least three legs 32. A number of legs greater than four as illustrated will add to the complexity and the cost of production without giving any advantages.

The invention claimed is:

1. A method of ensuring the desired mutual positioning of the main components of a femoral prosthesis during an operation for implantation thereof into a human patient, wherein said femoral prosthesis includes a prosthesis stem with a ball head neck and a cup that is adapted to be in the patient's pelvic cavity, wherein said cup comprises a recess linked with an exterior surface via a side face, in which the prosthesis stem is attached to a femur of the human patient, and the cup is placed on the pelvis of the human, said method comprising:
placing a tool on the neck of the prosthesis stem attached to the femur, wherein the tool comprises a guide ball configured for insertion into the recess of the cup and a support selected from the group consisting of an abutment surface and one or more legs, wherein the support is adapted for contact with at least a part of the side face of the cup that links the recess of the cup with the exterior surface of the cup;
controlling the mutual angle between the prosthesis stem and the cup with said tool, such that the prosthesis stem and cup are aligned at an optimum mutual angle defined by the contact of the support of the tool with the side face of the cup, wherein the femur that is undergoing surgery is then oriented in a pre-determined position; and placing the cup in its final desired position with the aid of the patient's femur, having said prosthesis stem attached thereto, and the tool placed on the implanted prosthesis stem for controlling the mutual angle between the prosthesis stem and the cup.

2. The method according to claim 1, wherein the femur is maintained in position until cement for fixing the cup has hardened.

3. A tool for use during an operation for implantation of a femoral prosthesis, said tool being configured to establish the mutual positioning of the main components in the femoral prosthesis upon assembly of the prosthesis components, wherein said femoral prosthesis includes a prosthesis stem with a neck, wherein the prosthesis stem is capable of being implanted in a patient's femur, and a cup that is adapted to be in the patient's pelvic cavity, wherein said cup comprises a recess linked with an exterior surface, via a side face, said tool comprising:

a cutout formed in the tool, wherein said cutout is designed to receive a part of the prosthesis stem and/or neck, a guide ball configured for insertion into the recess of the cup, and a support selected from the group consisting of an abutment surface and one or more legs, wherein the support is adapted for contact with at least a part of the side face of the cup that links the recess of the cup with the exterior surface of the cup; wherein the tool is adapted to be placed on the implanted prosthesis stem and configured to establish an optimal pre-determined mutual angle between the prosthesis stem and the cup in the pelvic cavity.

4. The tool according to claim 3, wherein the cutout comprises a bore designed for engagement with a part of the prosthesis stem.

5. The tool according to claim 3, wherein the cutout is designed for engagement with the neck of the prosthesis.

6. The tool according to claim 3, wherein the cutout is designed for engagement with a part of the prosthesis stem and the neck of the prosthesis.

7. The tool according to claim 3, wherein the one or more legs which abut at least a part of that part of the cup that links the exterior of the cup with the recess in the cup, are an integrated part of the guide ball.

8. The tool according to claim 3, wherein the one or more legs which abut at least a part of that part of the cup that links the exterior of the cup with the recess in the cup, are removably mounted on the guide ball.

9. The tool according to claim 3, wherein the support designed to abut at least a part of that part of the cup that links the exterior of the cup with the recess in the cup, comprises a collar with a diameter that is greater than that of the recess in the cup.

10. The tool according to claim 9, wherein the collar is mounted on the guide ball, such that said collar may be removed from said guide ball.

11. The tool according to claim 3, wherein the one or more legs comprise three or more legs designed to abut at least a part of that part of the cup that links the exterior of the cup with the recess in the cup.

12. The tool according to claim 11, wherein the legs can be retracted from abutment with the cup.

13. The tool according to claim 12, wherein the tool is adapted to be placed on a prosthesis stem temporarily implanted in the patient's femur.

14. A method of ensuring the desired mutual positioning of the main components of a femoral prosthesis during an operation for implantation thereof into a human patient, wherein said femoral prosthesis includes a prosthesis stem with a neck and a cup that is adapted to be in the patient's pelvic cavity, wherein said cup comprises a recess linked with an exterior surface via a side face, in which the prosthesis stem is attached to a femur of the human patient, and the cup is placed on the pelvis of the human, said method comprising:

placing a tool on the neck of the prosthesis stem attached to the femur, wherein the tool comprises a guide ball configured for insertion into the recess of the cup and a support selected from the group consisting of an abutment surface and one or more legs, wherein the support is adapted for contact with at least a part of the side face of the cup that links the recess of the cup with the exterior surface of the cup;

placing the cup on said tool such that at least part of the side face of the cup contacts the support and the guide ball is inserted in the recess;

controlling the mutual angle between the prosthesis stem and the cup with said tool, such that the prosthesis stem and cup are aligned at an optimum mutual angle defined by the contact of the support of the tool with the side face of the cup, wherein the femur that is undergoing surgery is then oriented in a pre-determined position; and placing the cup in its final desired position with the aid of the patient's femur, having said prosthesis stem attached thereto, and the tool placed on the implanted prosthesis stem for controlling the mutual angle between the prosthesis stem and the cup.

15. A tool for use during an operation for implantation of a femoral prosthesis, said tool being configured to establish the mutual positioning of the main components in the femoral prosthesis upon assembly of the prosthesis components, wherein said femoral prosthesis includes a prosthesis stem with a neck, wherein the prosthesis stem is capable of being implanted in a patient's femur, and a cup that is adapted to be in the patient's pelvic cavity, wherein said cup comprises a recess linked with an exterior surface, via a side face, said tool comprising:

a cutout formed in the tool, wherein said cutout is designed to receive a part of the prosthesis stem and/or neck, a support selected from the group consisting of an abutment surface and one or more legs, wherein the support is adapted for contact with at least a part of the side face of the cup that links the recess of the cup with the exterior surface of the cup, and a guide ball configured for insertion into the recess of the cup when at least a part of the side face of the cup contacts the support; wherein the tool is adapted to be placed on the implanted prosthesis stem and configured to establish an optimal pre-determined mutual angle between the prosthesis stem and the cup in the pelvic cavity.

* * * * *

UNITED STATES PATENT AND TRADEMARK OFFICE
CERTIFICATE OF CORRECTION

| | |
|---|---|
| PATENT NO. | : 8,070,822 B1 |
| APPLICATION NO. | : 10/099010 |
| DATED | : December 6, 2011 |
| INVENTOR(S) | : Bjørn Franc Iversen |

Page 1 of 1

It is certified that error appears in the above-identified patent and that said Letters Patent is hereby corrected as shown below:

In the Claims:

At column 6, line numbers 51-52, delete "ball head".

Signed and Sealed this
Twenty-first Day of May, 2013

Teresa Stanek Rea
*Acting Director of the United States Patent and Trademark Office*